United States Patent
Ramadhyani et al.

(10) Patent No.: US 11,786,285 B2
(45) Date of Patent: Oct. 17, 2023

(54) DUAL STAGE CRYOCOOLER

(71) Applicant: Biocompatibles UK Limited, Camberley (GB)

(72) Inventors: Satish Ramadhyani, Minneapolis, MN (US); Graig Kveen, Maple Grove, MN (US); Harishankar Natesan, Minneapolis, MN (US)

(73) Assignee: BIOCOMPATIBLES UK LIMITED, Surrey (GB)

(*) Notice: Subject to any disclaimer, the term of this patent is extended or adjusted under 35 U.S.C. 154(b) by 277 days.

(21) Appl. No.: 16/994,110

(22) Filed: Aug. 14, 2020

(65) Prior Publication Data
US 2021/0045793 A1    Feb. 18, 2021

Related U.S. Application Data

(60) Provisional application No. 62/886,853, filed on Aug. 14, 2019.

(51) Int. Cl.
*A61B 18/02* (2006.01)
*A61B 18/00* (2006.01)

(52) U.S. Cl.
CPC .... *A61B 18/02* (2013.01); *A61B 2018/00041* (2013.01); *A61B 2018/00577* (2013.01); *A61B 2018/0212* (2013.01)

(58) Field of Classification Search
CPC ............ A61B 18/02; A61B 2018/0041; A61B 2018/0212; A61B 2018/00577
See application file for complete search history.

(56) References Cited

U.S. PATENT DOCUMENTS 5,157,938 A * 10/1992 Bard ...................... F25B 17/083
  62/434
5,758,505 A *  6/1998 Dobak, III ................ F25B 9/02
  606/23

(Continued)

FOREIGN PATENT DOCUMENTS

CA    2332055 A1    11/1999
JP    05157397 H     6/1993

(Continued)

OTHER PUBLICATIONS

International Preliminary Report on Patentability received for PCT Patent Application No. PCT/US2020/046464, dated Feb. 24, 2022, 8 pages.

(Continued)

*Primary Examiner* — Ronald Hupczey, Jr.
*Assistant Examiner* — Abigail Bock
(74) *Attorney, Agent, or Firm* — Faegre Drinker Biddle & Reath LLP

(57) ABSTRACT

A cryoablation tool has a primary fluid circuit for cryogenically cooling or heating tissue surrounding the distal portion of the cryoablation tool. The primary fluid circuit has a primary-primary heat exchanger facilitating recuperative heat exchange between a high pressure stream of a primary fluid and a low pressure stream of the primary fluid. The cryoablation tool has a secondary fluid circuit having a secondary-secondary heat exchanger for permitting recuperative heat exchange between a high pressure stream of a secondary fluid and a low pressure stream of the secondary fluid. The secondary fluid circuit also has a primary-secondary heat exchanger permitting heat exchange between the high pressure stream of the primary fluid and the low pressure stream of the secondary fluid.

20 Claims, 4 Drawing Sheets

(56) References Cited

U.S. PATENT DOCUMENTS

| | | | | |
|---|---|---|---|---|
| 6,182,666 B1* | 2/2001 | Dobak, III | ............ | A61B 18/02 |
| | | | | 606/23 |
| 2004/0044334 A1* | 3/2004 | LaFontaine | ............ | A61B 18/02 |
| | | | | 606/21 |
| 2004/0211193 A1 | 10/2004 | Van Der Walt et al. | | |

FOREIGN PATENT DOCUMENTS

| | | | |
|---|---|---|---|
| JP | 11-276495 | H | 10/1999 |
| JP | 2002513907 | A | 5/2002 |
| WO | 2008/150289 | A1 | 12/2008 |

OTHER PUBLICATIONS

International Search Report and Written Opinion received for PCT Patent Application No. PCT/US2020/046464, dated Nov. 13, 2020, 11 pages.

* cited by examiner

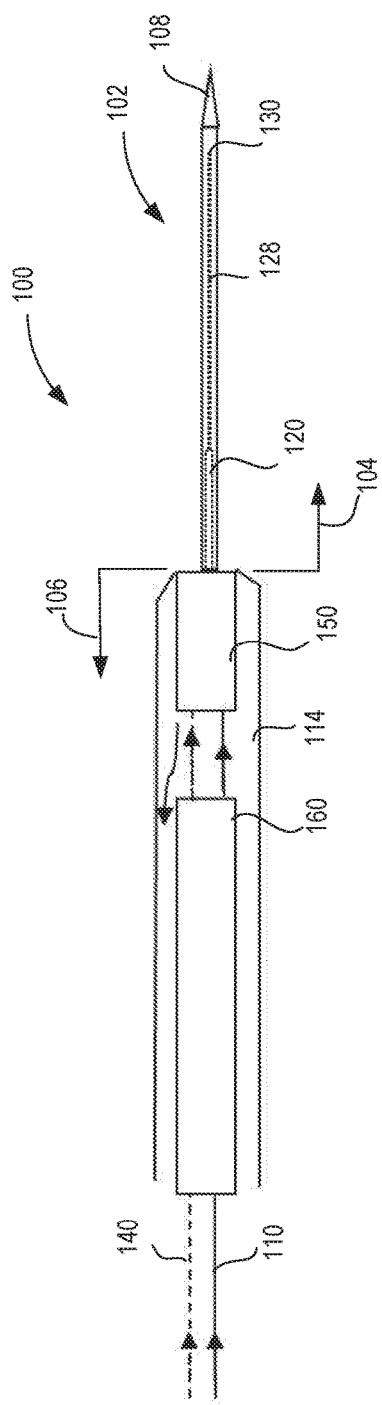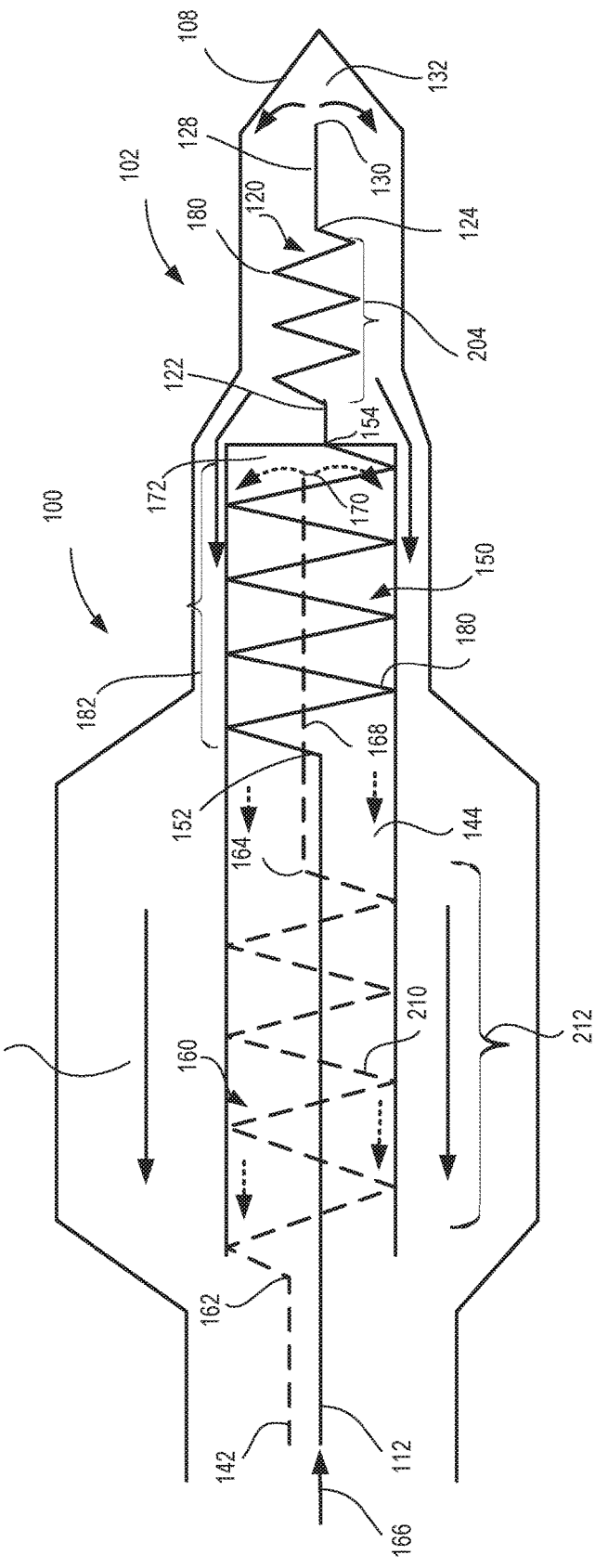

DUAL STAGE CRYOCOOLER

CROSS REFERENCE TO RELATED APPLICATION

This application claims priority to Provisional Application No. 62/886,853, filed Aug. 14, 2019, which is herein incorporated by reference in its entirety.

BACKGROUND

This disclosure relates to a cryoprobe for use in cryoablation and a system for cryoablation.

During cryosurgery, a surgeon may deploy one or more cryoprobes to ablate a target area of a patient anatomy by freezing and thawing the tissue. In one example, a cryoprobe uses the Joule-Thomson effect to produce cooling or heating of the probe tip. In such cases, the expansion of a cryofluid in the cryoprobe from a higher pressure to a lower pressure leads to cooling of the device tip to temperatures at or below those corresponding to cryoablating a tissue in the vicinity of the tip. Heat transfer between the expanded cryofluid and the outer walls of the cryoprobe leads to formation of an ice ball, in the tissue around the tip and consequent cryoablation the tissue.

Some cryoprobes may be useful for ablating lesions in a human lung or other body passageways. In such cases, the cryoprobes may have to navigate tortuous and/or narrow passageways, and accordingly may be constructed such that the cryoprobe may not support a cryofluid pressurized to pressures typical for cryoablation (e.g., 3500 psi). Further, delivering cryofluid at pressures lower than typical supply pressure for cryoablation (e.g., 3500 psi) may not result in sufficient cooling or formation of ice balls of desirable sizes within desirable times (e.g., 35 mm ice ball in 10 minutes).

SUMMARY

Advantageous aspects of the present disclosure provide a cryoablation tool with a two-stage cryocooler suitable for producing ice balls of sizes suitable for cryoablation.

In a first aspect of the cryoablation tool, a cryoablation tool is provided comprising: a primary fluid circuit comprising a flow of a high pressure stream of a primary fluid and a low pressure stream of the primary fluid, the primary fluid circuit being fluidly coupled to a distal portion of the cryoablation tool for cryogenically cooling or heating tissue surrounding the distal portion of the cryoablation tool, the primary fluid circuit comprising a primary-primary heat exchanger configured for recuperative heat exchange between the high pressure stream of the primary fluid and the low pressure stream of the primary fluid; a secondary fluid circuit comprising a high pressure region for flow of a high pressure stream of a secondary fluid and a low pressure region for flow of a low pressure stream of the secondary fluid, the secondary fluid circuit comprising a secondary-secondary heat exchanger for recuperative heat exchange between the high pressure stream of the secondary fluid and the low pressure stream of the secondary fluid, the secondary-secondary heat exchanger terminating in a secondary-secondary outlet; and a primary-secondary heat exchanger configured for recuperative heat exchange between the high pressure stream of the primary fluid and the low pressure stream of the secondary fluid, the primary-secondary heat exchanger comprising a primary-secondary inlet, the primary-secondary heat exchanger being arranged such that the primary-secondary inlet is positioned downstream of the secondary-secondary outlet along a direction of flow of the high pressure stream of the secondary fluid, the primary-secondary heat exchanger and the secondary-secondary heat exchanger arranged such that the low pressure stream of the secondary fluid exchanges heat with the primary fluid in the primary-secondary heat exchanger prior to exchanging heat with the high pressure stream of the secondary fluid in the secondary-secondary heat exchanger.

According to advantageous aspects, each of the primary-primary heat exchanger, the secondary-secondary heat exchanger and the primary-secondary heat exchanger comprises a tube having an outer wall. The outer wall of the tube comprises extensions to increase a surface area of the outer wall.

In another aspect, each of the primary-primary heat exchanger, the secondary-secondary heat exchanger and the primary-secondary heat exchanger comprises a finned tube.

In a further aspect, the secondary-secondary heat exchanger and the primary-secondary heat exchanger each comprises a tube that is wound in a series of turns about a tubular mandrel. In one approach, the secondary-secondary heat exchanger and the primary-secondary heat exchanger are each wound about the same tubular mandrel. The primary-primary heat exchanger may also comprise a tube that is wound in a series of turns about a tubular mandrel.

According to an aspect of this disclosure, the primary-primary heat exchanger is fluidly coupled with the primary-secondary heat exchanger such that the high pressure stream of the primary fluid flows through the primary-secondary heat exchanger prior to flowing through the primary-primary heat exchanger.

In another aspect, the fluid coupling between the primary-primary heat exchanger and the primary-secondary heat exchanger is configured to fluidly isolate the low pressure stream of the primary fluid from the primary-secondary heat exchanger.

In an additional aspect, the fluid coupling between the primary-primary heat exchanger and the primary-secondary heat exchanger is configured to fluidly isolate the low pressure stream of the primary fluid from the secondary-secondary heat exchanger.

In a further aspect, the flow of the low pressure stream of the primary fluid is isolated from the low pressure region of the secondary fluid circuit.

In a further aspect, the low pressure stream of the primary fluid may be arranged concentrically with the low pressure flow of the secondary fluid and is physically separated therefrom.

In a further aspect, the high pressure region of the primary-secondary heat exchanger and the high pressure region of the secondary-secondary heat exchanger are isolated from the low pressure stream of the primary fluid.

In a further aspect, both the secondary-secondary heat exchanger and the primary-secondary heat exchanger are isolated from the low pressure region of the primary fluid circuit.

According to an aspect, the primary fluid circuit comprises a first Joule-Thomson (J-T) orifice positioned in the distal section of the cryoablation tool, the first J-T orifice being fluidly coupled to the primary-primary heat exchanger via a primary supply conduit to receive the high pressure stream of the primary fluid after the high pressure stream of the primary fluid passes through the primary-primary heat exchanger, the first J-T orifice configured to cryogenically expand the high pressure stream of the primary fluid to the low pressure stream of the primary fluid.

In a further aspect, the cryoablation tool further comprises a primary return conduit for passage of the low pressure stream of the primary fluid therethrough, the first J-T orifice being disposed within the primary return conduit.

In certain aspects, the secondary fluid circuit comprises a second Joule-Thomson (J-T) orifice, the second J-T orifice being fluidly coupled to the secondary-secondary heat exchanger via a secondary supply conduit to receive the high pressure stream of the secondary fluid after the high pressure stream of the secondary fluid passes through the secondary-secondary heat exchanger, the second J-T orifice configured to cryogenically expand the high pressure stream of the secondary fluid to the low pressure stream of the secondary fluid.

In an additional aspect, the cryoablation tool further comprises a second return conduit to permit passage of the expanded secondary fluid, wherein, the secondary-secondary heat exchanger, the primary-secondary heat exchanger, and the second J-T orifice are each disposed within the second return conduit.

According to an aspect, the second return conduit is fluidly isolated from the low pressure stream of the primary fluid of the primary fluid circuit.

Further, the low pressure stream of the primary fluid and/or the secondary fluid may be configured to vent to atmosphere. A common vent conduit may be configured for the low pressure stream of the primary fluid and/or the secondary fluid to vent to the atmosphere (via the common vent conduit).

In an aspect, the cryoablation tool includes a primary inlet conduit for the primary fluid circuit to deliver the primary fluid to the primary fluid circuit, and a secondary inlet conduit to deliver the secondary fluid to the secondary fluid circuit. The common vent conduit may be arranged to pass the primary fluid or the secondary fluid over the primary inlet conduit and the secondary inlet conduit before venting the primary fluid or the secondary fluid to the atmosphere.

A further embodiment provides A cryoablation tool comprising: a shaft having a proximal end and a distal end; a primary supply conduit configured to supply a primary fluid from a high-pressure cryogenic gas source to a distal end of the shaft, the primary supply conduit having a first Joule-Thomson orifice at a distal end thereof, configured to deliver the primary fluid to a first expansion chamber; a primary return conduit configured to carry the primary fluid away from the distal expansion chamber; a secondary supply conduit configured to supply a secondary fluid to a second Joule-Thomson orifice, the second J-T orifice configured to deliver the secondary fluid to a second expansion chamber; a secondary return conduit configured to carry the secondary fluid away from the second expansion chamber; the primary supply conduit comprising a primary-secondary heat exchange region and a primary-primary heat exchange region, the primary-primary heat exchange region being down stream of the primary-secondary heat exchange region; and the secondary supply conduit comprising a secondary-secondary heat exchange region up stream of the second J-T orifice; the primary fluid return conduit further configured to pass the primary cryogenic gas over the primary-primary heat exchange region, in counterflow to the supply direction; the secondary return conduit further configured to pass the secondary fluid sequentially over the primary-secondary heat exchange region and the secondary-secondary heat exchange region in counterflow to the supply direction in each case.

In a further aspect, the primary supply conduit is arranged in a first plurality of coils, configured as a primary-secondary heat exchanger within the primary-secondary heat exchange region and a second plurality of coils, configured as a primary-primary heat exchanger, within the primary-primary heat exchange region; and the secondary supply conduit being arranged in a third plurality of coils configured as a secondary-secondary heat exchanger within the secondary-secondary heat exchange region.

In a further aspect, the primary return conduit is configured to pass the expanded primary fluid over the primary-primary heat exchanger; and the secondary return conduit is configured to pass the expanded secondary fluid over the primary-secondary heat exchanger prior to passing the expanded secondary fluid over the secondary-secondary heat exchanger.

In a further aspect, the first plurality of coils comprises a first coil and a second coil, the first coil arranged upstream of the second coil relative to the direction of primary fluid flow through the first coil; each coil of the second plurality of coils being positioned downstream of the said second coil relative to the direction of primary fluid flow in the first coil; and each coil of the third plurality of coils is positioned upstream of the first coil relative to the direction of primary fluid flow in the said first coil.

In a further aspect, the secondary return conduit may be configured to pass the expanded secondary fluid, sequentially over the full length of the primary-secondary heat exchange region before passing the secondary fluid over the full length of the secondary-secondary heat exchange region. The secondary return conduit may be configured to pass the expanded secondary fluid over each coil of the primary-secondary heat exchanger before passing it over the secondary to secondary heat exchanger.

In a further aspect the primary-primary heat exchange region is arranged within the primary return conduit and is further, arranged distally of both the primary-secondary and the secondary-secondary heat exchange regions.

In a further aspect the secondary-secondary heat exchange region is arranged proximally to the primary-secondary heat exchange region, within the secondary return conduit.

In a further aspect the primary supply conduit comprises a tubular region wound in a series of turns about a mandrel to form the primary-secondary heat exchanger. The secondary supply conduit may comprise a tubular region wound in a series of turns about a mandrel to form the secondary-secondary heat exchanger. Further, the primary supply conduit may comprise a tubular region wound in a series of turns about a mandrel to form the primary-secondary heat exchanger, and the secondary supply conduit may comprise a tubular region wound in a series of turns about the same mandrel to form the secondary-secondary heat exchanger. The primary supply conduit may comprise a tubular region wound in a series of turns about a mandrel to form the primary-primary heat exchanger.

In a further aspect the primary return conduit is configured to pass the primary fluid over the primary-primary heat exchange region but not the primary-secondary heat exchange region or the secondary-secondary heat exchange region.

In a further aspect the primary-secondary heat exchange region and the secondary-secondary heat exchange region are each disposed within the secondary return conduit. The secondary return conduit may then fluidly isolate the primary return conduit from the primary-secondary heat exchange region and the secondary-secondary heat exchange region.

In a further aspect the primary return conduit comprises a portion disposed concentrically about the secondary return conduit. This portion may be downstream of the primary-primary heat exchange region with respect to the direction of expanded primary fluid flow.

In a further aspect the primary return conduit is configured to vent the primary fluid to atmosphere and/or the secondary return conduit is configured to vent the secondary fluid to atmosphere.

BRIEF DESCRIPTION OF DRAWINGS

FIG. 1 is an exemplary schematic of a cryoablation tool;

FIG. 2 is another exemplary schematic of the cryoablation tool of FIG. 1 illustrating interior details thereof;

DETAILED DESCRIPTION

Figure 3:
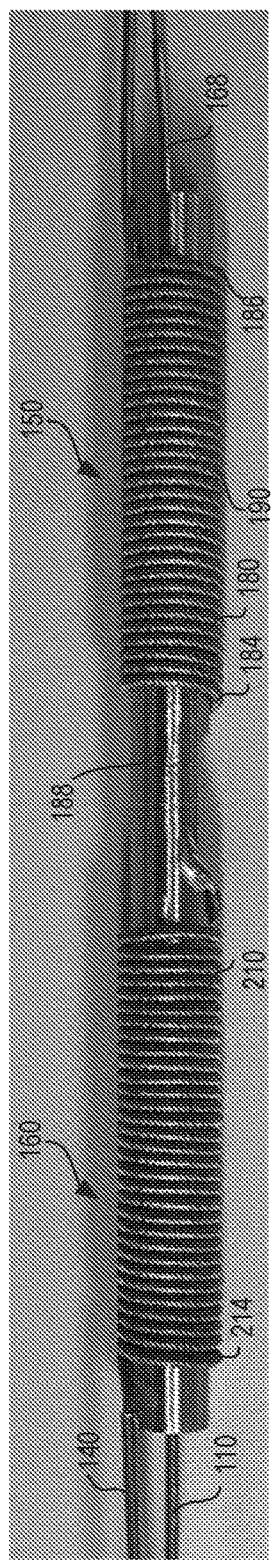
FIG. 3 is a pictorial view of an exemplary precooler of the cryoablation tool of FIG. 1.

FIG. 1 illustrates a schematic of a cryoablation tool 100 according to an embodiment. According to some embodiments, the cryoablation tool 100 may include a catheter 102. In advantageous aspects, the catheter 102 may be inserted into a working channel of a bronchoscope, and may, therefore be, generally flexible. The cryoablation tool 100 may include a distal section 104 and a proximal section 106. The distal section 104 may terminate in a distal operating tip 108. In some instances, the distal operating tip 108 may have to pierce tissue, and therefore, may be configured as a rigid tip. Alternatively, the distal operating tip 108 may not be a rigid tip.

With reference to FIGS. 1 and 2, the cryoablation tool 100 includes a primary fluid circuit 110 (shown in solid lines) 110. The primary fluid circuit 110 may be associated with a primary fluid. The primary fluid circuit 110 may be in fluid communication with the distal section 104 of the cryoablation tool 100. The primary fluid may cool (e.g., cryogenically) or heat tissue surrounding the distal portion of the cryoablation tool 100. The primary fluid circuit 110 may include a primary supply conduit 112 for carrying a high pressure stream of the primary fluid. The primary fluid circuit 110 may also include a primary return conduit 114 for carrying a low pressure stream of the primary fluid.

The primary fluid circuit 110 may also include a primary-primary heat exchanger 120 configured for heat exchange (e.g., recuperative heat exchange) between the high pressure stream of the primary fluid and the low pressure stream of the primary fluid. The primary-primary heat exchanger 120 includes a primary-primary inlet 122 and a primary-primary outlet 124. The primary-primary inlet 122 may be fluidly coupled to the primary supply conduit 112 to receive the high pressure stream of the primary fluid. The primary-primary outlet 124 may be fluidly coupled to a primary conduit 128 (e.g., a primary capillary tube) to deliver the primary fluid toward the distal operating tip 108.

In advantageous aspects, the high pressure stream of the primary fluid (from the primary supply conduit 112) may flow through a first cryocooler 130. In such embodiments, the high pressure stream of the primary fluid may be upstream (with respect to direction 166) of the first cryocooler 130. Further, the low pressure stream of the primary fluid may be downstream (with respect to direction 166) of the first cryocooler 130. As illustrated in FIG. 2, the primary supply conduit 128 (e.g., primary capillary tube) comprises a first Joule-Thomson ("J-T") orifice 130 downstream of the primary-primary outlet, at the end of the primary supply conduit. Accordingly, the first cryocooler 130 can be an open loop cryocooler, such as the first J-T orifice 130.

In such embodiments, the high pressure stream of the primary fluid may undergo expansion at or downstream of the first J-T orifice 130 in a first expansion chamber 132. The first expansion chamber 132 may be in fluid communication with the primary return conduit 114 to carry the (expanded low pressure stream of) the primary fluid away from the expansion chamber, toward the proximal section 106 (e.g., to vent to atmosphere, if the primary fluid circuit 110 is an open circuit, or back to a primary fluid source if the primary fluid circuit 110 is a closed circuit).

The primary fluid can be a cooling fluid (e.g., nitrogen, air, argon, krypton, xenon, $N_2O$, $CO_2$, $CF_4$) in embodiments. In such cases, the high pressure stream of the primary fluid may be at a pressure such that expansion via the first J-T orifice 130 may result in the primary fluid cooling to temperatures for cryogenically ablating tissue surrounding the distal operating fluid. In certain aspects, the pressure of the high pressure stream of the primary fluid upstream of the first J-T orifice 130 can be between about 1000 psi and about 2000 psi (e.g., about 1800 psi). Accordingly, in the embodiments where the primary fluid is a cooling fluid, the temperature of the primary fluid after expansion from the first J-T orifice 130 can be less than about 190 Kelvin.

Alternatively, the primary fluid can be a heating fluid (e.g., helium, hydrogen). In such cases, the high pressure stream of the primary fluid may be at a pressure such that expansion via the first J-T orifice 130 may result in a temperature increase of the primary fluid, correspondingly resulting in heating of tissue surrounding the distal operating fluid. Such embodiments may be useful for thawing frozen tissue.

In some embodiments, the primary fluid circuit 110 may be arranged such that the flow of the high pressure stream of the primary fluid is countercurrent to the flow of the low pressure stream of the primary fluid over at least certain portions of the primary fluid circuit 110. For instance, as mentioned above, in an embodiment, the high pressure stream of the primary fluid passes through a first J-T orifice 130. As illustrated in FIGS. 1 and 2, the flow direction of the primary fluid is reversed upon expansion at the first J-T orifice 130, thereby resulting in countercurrent flow of the high pressure stream of the primary fluid and the low pressure stream of the primary fluid near the first J-T orifice 130. Furthermore, the high pressure stream of the primary fluid and the low pressure stream of the primary fluid may be in countercurrent flow near the primary-primary inlet 122 of the primary-primary heat exchanger 120, so the primary return conduit is configured to pass the primary cryogenic gas over the primary-primary heat exchange region, in counterflow to the supply direction.

According to advantageous aspects, the countercurrent arrangement of the high pressure stream of the primary fluid and the low pressure stream of the primary fluid may permit recuperative heat exchange therebetween. In instances where the primary fluid circuit 110 carries a cooling gas, the recuperative heat exchange may include heat removal from the high pressure stream of the primary fluid leading to precooling of the primary fluid prior to expansion via the first J-T orifice 130. In instances where the primary fluid circuit 110 carries a heating gas, the recuperative heat exchange may include heat addition from the high pressure stream of the primary fluid leading to preheating of the primary fluid prior to expansion via the first J-T orifice 130. The recuperative heat exchange may advantageously lead to reaching desired temperatures at the distal operating tip 108.

As described previously, in some embodiments, the cryoablation tool 100 may include a catheter 102 sufficiently flexible to be maneuvered within a bronchoscope. In such embodiments, the catheter 102 may be made of materials that may not be able to withstand typical pressures at which the primary fluid may be supplied in other cryoablation tools (e.g., greater than about 2000 psi, for instance, about 3500 psi). Under such circumstances, it may be advantageous to supply the primary fluid at pressures less than typical pressures for cryoablation. The primary fluid may be supplied at less than about 2000 psi, for instance, about 1800 psi). However, to facilitate temperatures suitable for cryoablation from being reached at the distal operating tip 108, a secondary fluid circuit 140 may be provided to precool the primary fluid, as will be described further below.

Referring to FIGS. 1 and 2, the cryoablation tool 100 includes a secondary fluid circuit 140 (shown in dotted lines). The secondary fluid circuit 140 may include a secondary supply conduit 142, which carrys a high pressure stream of a secondary fluid. The secondary supply conduit is configured to supply a second fluid to a second cryocooler (J-T orifice). The second cryocooler may be configured to deliver the second fluid to a second expansion chamber. The secondary fluid circuit 140 may also include a secondary return conduit 144 which carries a low pressure stream of the secondary fluid. The secondary return conduit may be configured to carry the second fluid away from the second expansion chamber.

In advantageous aspects, the secondary fluid circuit 140 may facilitate heat exchange between the primary fluid and the secondary fluid. In some such advantageous aspects, the secondary fluid circuit 140 can be used to precool the high pressure stream of the primary fluid in embodiments where the primary fluid cools upon expansion to cryogenically ablate tissue surrounding the distal operating tip 108. In such advantageous aspects, referencing FIG. 2, the secondary fluid circuit 140 may also include a primary-secondary heat exchanger 150. In certain aspects, the primary-secondary heat exchanger 150 may facilitate heat exchange between the high pressure stream of the primary fluid and the low pressure stream of the secondary fluid. The primary-secondary heat exchanger 150 may include a primary-secondary inlet 152, and a primary-secondary outlet 154.

With continued reference to FIG. 2, the secondary fluid circuit 140 may include a secondary-secondary heat exchanger 160 that permits heat exchange between the high pressure stream of the secondary fluid and the low pressure stream of the secondary fluid (e.g., recuperative heat exchange). In some advantageous aspects, the secondary fluid may also be a cooling fluid. In such embodiments, recuperative heat exchange between the high pressure stream of the secondary fluid and the low pressure stream of the secondary fluid may remove heat from the high pressure stream of the secondary fluid. Accordingly, the secondary-secondary heat exchanger 160 may facilitate precooling the high pressure stream of the secondary fluid.

Referring again to FIG. 2, the secondary-secondary heat exchanger 160 may include a secondary-secondary inlet 162 and a secondary-secondary outlet 164. The secondary-secondary inlet 162 may be upstream of the secondary-secondary outlet 164, along a direction 166. Further, the secondary-secondary inlet 162 may be upstream of each of the primary-primary inlet 122, and the primary-primary outlet 124. Additionally, the secondary-secondary outlet 164 may also be upstream of each of the primary-primary inlet 122, and the primary-primary outlet 124.

The secondary-secondary inlet 162 may be fluidly coupled to the secondary supply conduit 142 to receive the high pressure stream of the secondary fluid. The secondary-secondary outlet 164 may be fluidly coupled to a secondary conduit 168 (e.g., a secondary capillary tube 168) to receive the secondary fluid from the secondary-secondary outlet 164. The secondary fluid may thus pass through the secondary-secondary heat exchanger 160 by entering at the secondary-secondary inlet 162, and exiting at the secondary-secondary outlet 164.

In advantageous aspects, the high pressure stream of the secondary fluid leaving the secondary-secondary outlet 164 may enter the secondary capillary tube 168, and may flow through a second cryocooler 170. In such embodiments, the high pressure stream of the secondary fluid may be upstream (with respect to direction 166) of the second cryocooler 170. Further, the low pressure stream of the secondary fluid may be downstream (with respect to direction 166) of the second cryocooler 170. In the illustrated embodiment of FIG. 2, the secondary conduit 168 (e.g., secondary capillary tube 168) downstream of the secondary-secondary outlet 164 terminates in a second Joule-Thomson ("J-T") orifice 170. Accordingly, the second cryocooler 170 can be the second J-T orifice 170. In such embodiments, the high pressure stream of the secondary fluid may undergo expansion at or downstream of the second J-T orifice 170 in a second expansion chamber 172. The second expansion chamber 172 may be in fluid communication with the secondary return conduit 144 to carry the expanded low pressure stream of the secondary fluid (e.g., to vent to atmosphere, if the secondary fluid circuit 140 is an open circuit, or back to a secondary fluid source if the secondary fluid circuit 140 is a closed circuit).

In some embodiments, the secondary fluid circuit 140 may be arranged such that the flow of high pressure stream of the secondary fluid is countercurrent to the flow of the low pressure stream of the secondary fluid over at least certain portions of the secondary fluid circuit 140. For instance, as mentioned above, in an embodiment, the high pressure stream of the secondary fluid passes through a second J-T orifice 170. As illustrated in FIGS. 1 and 2, the flow direction of the secondary fluid is reversed upon expansion at the second J-T orifice 170, thereby resulting in countercurrent flow of the high pressure stream of the secondary fluid and the low pressure stream of the secondary fluid near the second J-T orifice 170. Furthermore, the high pressure stream of the secondary fluid and the low pressure stream of the secondary fluid may be in countercurrent flow near the secondary-secondary inlet 162 of the secondary-secondary heat exchanger 160. Thus in an advantageous aspect, the secondary return conduit 144 may be configured to pass the secondary fluid sequentially over the primary-secondary heat exchange region 182 and the secondary-secondary heat exchange region 212 in counterflow to the supply direction in each case.

As illustrated in FIG. 2, the primary-secondary heat exchanger 150 may be arranged sequentially with respect to the secondary-secondary heat exchanger 160. Such a sequential arrangement may facilitate the low pressure stream of the secondary fluid to exchange heat with the primary fluid in the primary-secondary heat exchanger 150 prior to exchanging heat with the high pressure stream of the secondary fluid in the secondary-secondary heat exchanger 160. In such a sequential arrangement, the primary-secondary inlet 152 may be positioned downstream (with respect to direction 166) of the secondary-secondary outlet 164. Further, the primary-secondary outlet 154 may also be positioned downstream (with respect to direction 166) of the secondary-secondary outlet 164.

In certain aspects, the expanded low pressure stream of secondary fluid may first exchange heat with the high pressure stream of the primary fluid. For instance, in an embodiment (described further below), the secondary stream may flow over the primary-secondary heat exchanger 150 entirely before flowing over the secondary-secondary heat exchanger 160. Thus the secondary return conduit may be configured to pass the expanded secondary fluid, sequentially over the entire primary-secondary heat exchange region (or each coil of the primary to secondary heat exchange coils before passing the secondary fluid over the secondary-secondary heat exchange coils.

Referring back to FIGS. 1 and 2, in certain embodiments in which the cryoablation tool 100 includes a flexible catheter 102, the secondary-secondary heat exchanger 160 and the primary-secondary heat exchanger 150 may each be positioned outside the catheter 102, for instance, near the proximal section 106 of the cryoablation tool 100. Further, the primary-primary heat exchanger 120 may be located within the flexible catheter 102. This arrangement may further facilitate supplying the secondary fluid at pressures greater than the high pressure stream of the primary fluid.

As described previously, in embodiments where the cryoablation tool 100 includes a flexible catheter 102, it may be advantageous to supply the primary fluid at pressures less than typical pressures for cryoablation. For instance, the primary fluid may be supplied at less than about 2000 psi, for instance, about 1800 psi, which, in the absence of the secondary fluid circuit 140, may not result in sufficient cooling for cryoablation if the primary fluid is a cooling fluid. However, by passing the primary fluid through the primary-secondary heat exchanger 150, recuperative heat exchange can be permitted between the secondary fluid to precool the primary fluid and achieve temperatures suitable for cryoablation even when the primary fluid is supplied at pressures less than the typical supply pressure for cryoablation.

Advantageously, the high pressures stream of the secondary fluid may be at a pressure greater than a pressure of the high pressure stream of the primary fluid. The secondary fluid may, for instance, be supplied at pressures greater than about 2000 psi (e.g., 3500 psi). As the secondary fluid passes through the second cryocooler 170 (e.g., second J-T orifice 170), the secondary fluid may reach cryogenic temperatures (e.g., less than about 190 Kelvin) if the secondary fluid is a cooling fluid. The expanded low pressure stream of the secondary fluid may remove heat from the high pressure stream of the primary fluid in the primary-secondary heat exchanger 150, thereby precooling the primary fluid prior to the primary fluid's passage through the primary-primary heat exchanger 120.

Figure 4:
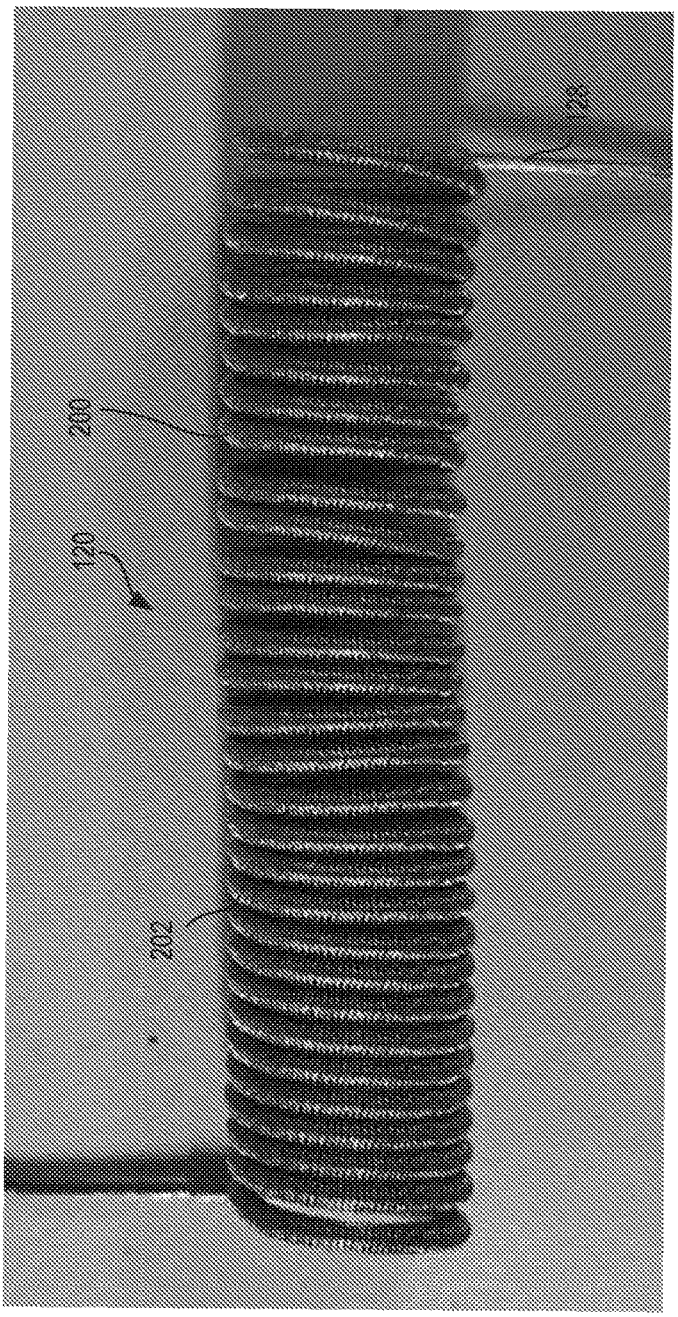
FIG. 4 is a pictorial view of an exemplary primary-primary heat exchanger of the cryoablation tool of FIG. 1.

FIG. 3 illustrates pictorial views of the primary-secondary and secondary-secondary heat exchangers according to an embodiment. FIG. 4 illustrates a pictorial view of the primary-primary heat exchanger 120 according to an embodiment.

Referencing FIG. 3, the primary supply conduit 112 may be a metal tube that may be fluidly coupled to the primary-secondary heat exchanger 150. The primary-secondary heat exchanger 150 may include a plurality of first heat exchange coils 180 between the primary-secondary inlet 152 and the primary-secondary outlet 154.

Referring to FIGS. 2 and 3, the plurality of first heat exchanger coils may define a first heat exchanger region 182. The plurality of coils may include a first coil 184 and a second coil 186. The first coil 184 may be upstream of the second coil 186 (with respect to direction 166). The first coil 184 may be more proximal to the primary-secondary inlet 152 than to the primary-secondary outlet 154. The second coil 186 may be more proximal to the primary-secondary outlet 154 than to the primary-secondary inlet 152. The primary-secondary heat exchange region may extend between the first coil 184 and the second coil 186 and/or between the primary-secondary inlet 152 and the primary-secondary outlet 154.

According to certain embodiments, the plurality of first heat exchanger coils 180 (primary-secondary heat exchanger) may be formed from a metal tube (a tubular region of the primary supply conduit) wound about a mandrel 188. The metal tube may include an outer wall. The outer wall may include extensions to increase a surface area of the outer wall. For instance, in an embodiment, the first heat exchange coils 180 may include fins 190 to increase heat exchange over the first heat exchanger region 182. The primary fluid may flow through an interior of the metal tube. Referring to FIGS. 2 and 3, the expanded low pressure stream of primary fluid may flow over the finned portions of the metal tube. The fins 190 may enhance heat exchange between the high pressure stream of the primary fluid flowing through the interior of the metal tube, and the low pressure stream of the secondary fluid flowing over the exterior of the finned portions of the metal tube.

Referencing FIG. 2, the primary fluid, after exchanging heat with the secondary fluid in the primary-secondary exchanger, may continue toward the primary-primary heat exchanger 120. Referring to FIG. 4, the primary-primary heat exchanger 120 may include a plurality of second heat exchange coils 200. With reference to FIGS. 2 and 4, the primary-secondary heat exchanger 150 and the primary-primary heat exchanger 120 may be in a sequential arrangement. Thus, each coil of the plurality of second heat exchange coils 200 may be downstream (with respect to direction 166) of the first coil 184 of the plurality of first heat exchange coils 180.

According to certain embodiments, the plurality of second heat exchange coils 200 (primary-primary heat exchanger) may be formed from a metal tube (tubular region of the primary supply conduit) wound about a mandrel (e.g., analogous to the mandrel 188 of FIG. 3). Returning to FIG. 4, the metal tube may include an outer wall. The outer wall may include extensions to increase a surface area of the outer wall. For instance, in an embodiment, the second heat exchange coils 200 may include fins 202 to increase heat exchange over the second heat exchanger region 204. The primary fluid may flow through an interior of the metal tube. Referring to FIGS. 2 and 3, the expanded low pressure stream of primary fluid may flow over the finned portions of the metal tube. The fins 202 may enhance heat exchange between the high pressure stream of the primary fluid flowing through the interior of the metal tube, and the low pressure stream of the primary fluid flowing over the exterior of the finned portions of the metal tube.

The primary fluid leaving the primary-primary heat exchanger 120 may enter the primary conduit 128 (e.g., primary capillary tube), and flow toward the first cryocooler 130, as described previously. The first cryocooler 130 may, in some instances, be a first J-T orifice 130. The primary fluid may expand in the primary expansion chamber positioned downstream of the primary-primary heat exchange region near the distal operating tip 108 for expansion of the primary fluid. The expanded low pressure primary fluid may be carried by the primary return conduit 114.

Referring again to FIGS. 2 and 4, the second heat exchange region (the primary-primary heat exchange region) 204 may be arranged within the primary return conduit 114. Thus the primary return conduit 114 may generally surround the plurality of second heat exchange coils (second heat exchange region) 200. The primary return conduit 114 may thus pass the expanded low pressure primary fluid over the second heat exchange region and thereby exchange heat (e.g., recuperative heat exchange) with the high pressure stream of primary fluid flowing in the interior of the metal tube of the plurality of second heat exchange coils 200 (primary-primary heat exchanger).

Advantageously, as illustrated in FIG. 2, the primary return conduit 114 is configured to pass the primary fluid over the primary-primary heat exchange region 204 but not the primary-secondary heat exchange region 182 or the secondary-secondary heat exchange region 212. Advantageously, the primary-secondary heat exchange region 182 and the secondary-secondary heat exchange region 212 are each disposed within the secondary return conduit 144, the secondary return conduit fluidly isolating the expanded primary fluid flowing in the primary return conduit 114 from the primary-secondary heat exchange region 182 and the secondary-secondary heat exchange region 212. Advantageously the primary return conduit 114 may comprise a portion disposed concentrically about the secondary return conduit 144. This enables the flow or primary fluid to pass around the secondary return conduit 144 without passing over either of the primary secondary 182 or the secondary-secondary 212 heat exchange regions disposed within the secondary return conduit 144. Advantageously this portion is down stream of the primary-primary heat exchange region 204, with respect to primary fluid flow.

With reference to FIGS. 2 and 3, the secondary supply conduit 142 may supply the secondary fluid to the secondary-secondary heat exchanger 160. The secondary-secondary heat exchanger 160 may include a plurality of third heat exchange coils 210 that may define a secondary-secondary heat exchange region 212.

According to certain illustrated embodiments, the plurality of third heat exchanger coils (secondary-secondary heat exchanger) may be formed from a metal tube (tubular portion of the second supply conduit) wound about a mandrel. In some cases, the mandrel about which the third heat exchanger coils may be wound may either be identical to, or in the alternative, coextensive with the mandrel 188 about which the first heat exchanger coils may be wound. Alternatively, the mandrel about which third heat exchanger coils may be wound may be separate from the mandrel 188 of about which the first heat exchanger coils may be wound.

Returning to FIG. 3, the metal tube of the third heat exchange coils 210 may include an outer wall. The outer wall may include extensions to increase a surface area of the outer wall. For instance, in an embodiment, the third heat exchange coils 210 may include fins 214 to increase heat exchange over the third heat exchanger region. The secondary fluid entering the secondary-secondary inlet 162 may flow through an interior of the metal tube. Referring to FIGS. 2 and 3, the expanded low pressure stream of secondary fluid (leaving the second J-T orifice 170) may flow over the finned portions of the metal tube. The fins 214 may enhance heat exchange between the high pressure stream of the secondary fluid flowing through the interior of the metal tube, and the low pressure stream of the secondary fluid flowing over the exterior of the finned portions of the metal tube.

As described previously, the low pressure stream of the secondary fluid may first exchange heat with the high pressure stream of the primary fluid in the primary-secondary heat exchanger 150, prior to exchanging heat with the high pressure stream of the secondary fluid in the secondary-secondary heat exchanger 160. Accordingly, the each coil of the plurality of third heat exchange coils 210 may be positioned upstream of the first coil 184 of the plurality of first heat exchange coils 180. Thus the secondary-secondary heat exchange region 212 and primary-secondary heat exchange region 182 may be arranged within the secondary return conduit 144 and the secondary-secondary heat exchange region 212 may be arranged downstream to the primary-secondary heat exchange region 182, with respect to the flow direction within the secondary return conduit 144.

The secondary fluid leaving the secondary-secondary heat exchanger 160 may enter the secondary conduit 168 (e.g., secondary capillary tube 168), and flow toward the second cryocooler 170, as described previously. The second cryocooler 170 may, in some instances, be the second J-T orifice 170. The secondary fluid may expand in the secondary expansion chamber positioned downstream of the primary-secondary heat exchange region. Upon expansion, the low pressure stream of the secondary fluid flows over the finned portion of the primary-secondary heat exchange region for recuperative heat exchange with the high pressure stream of the primary fluid. The low pressure stream of the secondary fluid then flows over the finned portion of the secondary-secondary heat exchange region 212 for recuperative heat exchange with the high pressure stream of the secondary fluid.

Advantageously, in the instances where the primary fluid and the secondary fluid are each cooling fluids, the secondary fluid may reach cryogenic temperatures after flowing through the second cryocooler 170. As the secondary fluid flows over the finned tube of the first heat exchange coils 180, the temperature of the secondary fluid may gradually increase. The secondary fluid flowing over the finned tube of the third heat exchange coils 210 (e.g., near the secondary-secondary outlet 164) may thus be at a higher temperature than the temperature of the secondary fluid flowing just proximal to the primary-secondary outlet 154. Thus, by passing the secondary fluid first over the primary-secondary heat exchanger 150, the secondary fluid at its coldest temperature may be in heat exchange with the primary fluid, thereby permitting optimal heat removal from the primary fluid for effective precooling thereof.

Referring again to FIG. 2, the secondary return conduit 144 may generally surround the plurality of third heat exchange coils 210. Advantageously, the secondary return conduit 144 may be fluidly isolated from the primary return conduit 114, so as to fluidly isolate the low pressure stream of the primary fluid from the low pressure stream of the secondary fluid. Thus, the low pressure stream of the primary fluid may not flow over the secondary-secondary heat exchanger 160 or over the primary-secondary heat exchanger 150.

According to advantageous embodiments, the primary-secondary heat exchange region, the primary-primary heat exchange region and the secondary-secondary heat exchange region 212 may be longitudinally (e.g., along direction 166) separated from each other. Referencing FIGS. 2-4, each coil of the secondary-secondary heat exchange region 212 may be upstream of the primary-secondary heat exchange region and the primary-primary heat exchange region. Further, the distance between adjacent coils of the plurality of third heat exchange coils 210 may be substantially less than the distance between a coil of the secondary-secondary heat exchange region 212 and a coil of the primary-secondary heat exchange region or a coil of the primary-primary heat exchange region.

Continuing with FIGS. 2-4, each coil of the plurality of third heat exchange coils 210 (forming the secondary-secondary heat exchanger 160) may be upstream (with respect to direction 166) of each of the primary-secondary inlet 152 and the primary-primary inlet 122. Further, each coil of the plurality of first coils (forming the primary-secondary heat exchanger 150) may be upstream (with respect to direction 166) of the primary-primary inlet 122.

Arrangements such as those disclosed above may facilitate effective recuperative heat exchange, thereby permitting desired cryoablation (or thawing) properties at the distal operating tip 108, as described previously.

EXAMPLE

Figure 5:
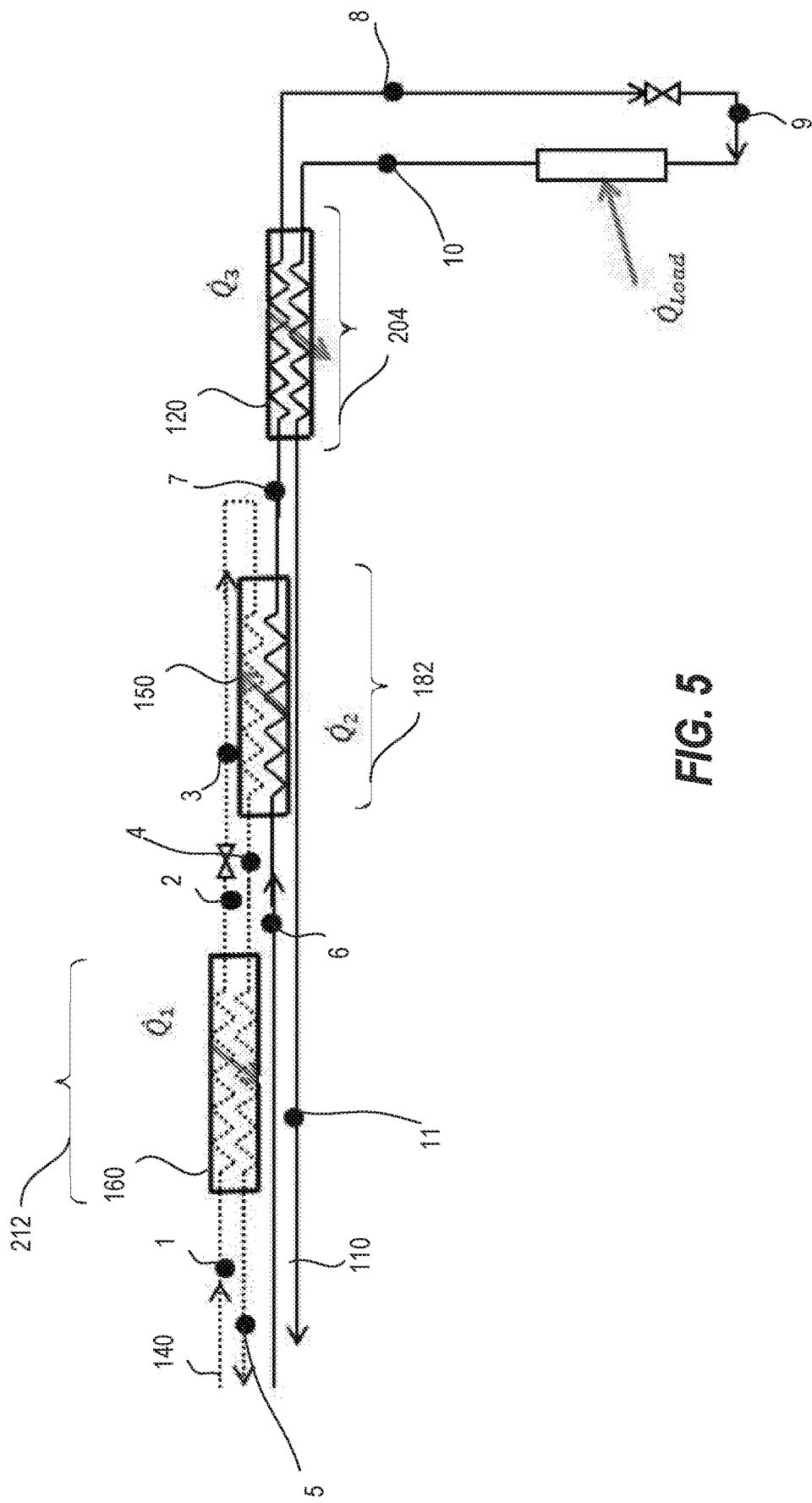
FIG. 5 is a thermodynamic schematic illustrating the primary-primary, primary-secondary and secondary-secondary heat exchangers associated with the cryoablation tool of FIG. 1.
Figure 6:
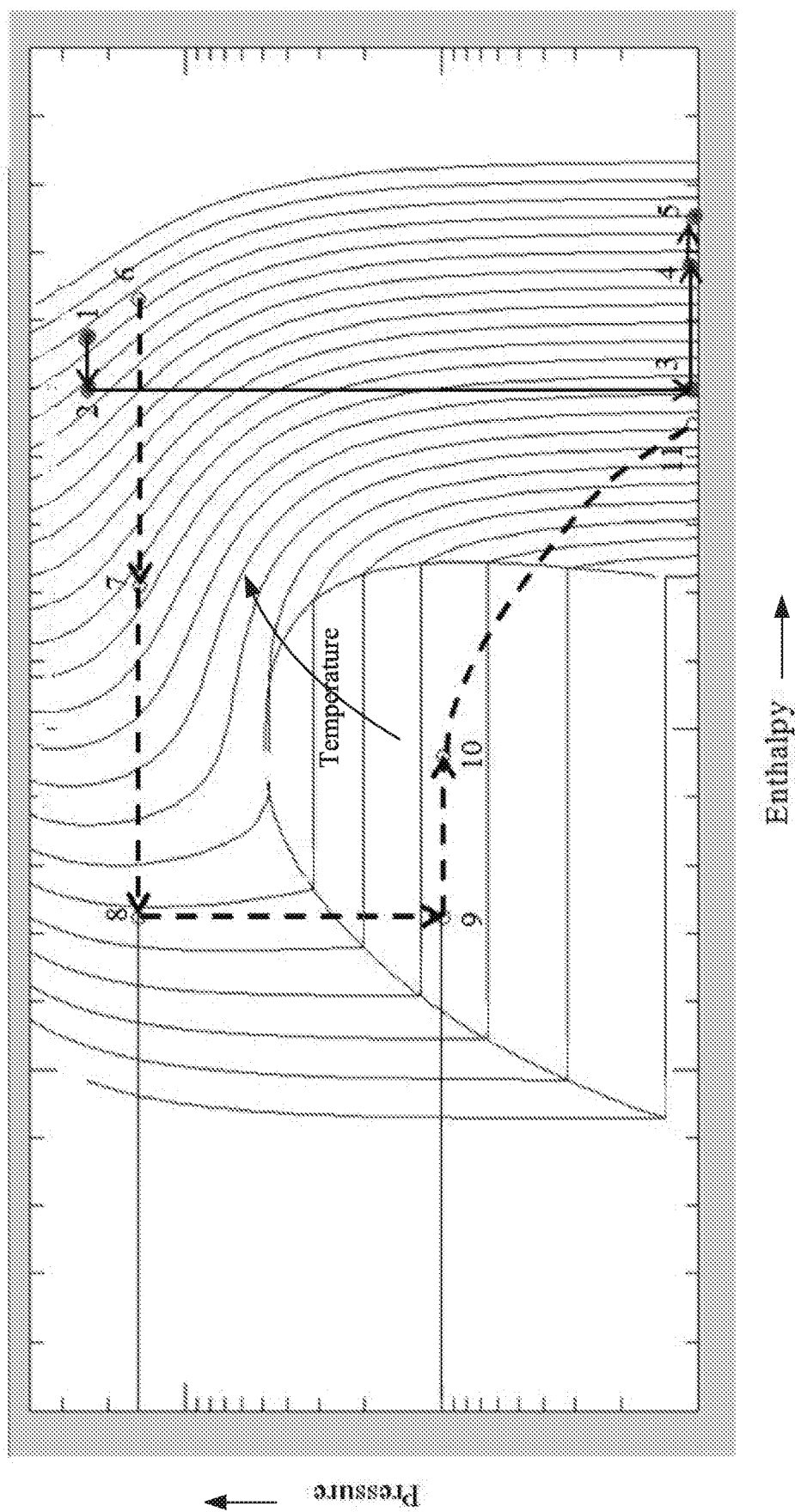
FIG. 6 is an exemplary thermodynamic property diagram illustrating the thermodynamic states associated with the primary-primary, primary-secondary and secondary-secondary heat exchangers illustrated in FIG. 1.

FIGS. 5 and 6 illustrate a thermodynamic schematic and a thermodynamic property diagram to illustrate an example of the dual stage cryocooler. According to the example, the primary fluid can be argon. The secondary fluid can also be argon. Referencing FIG. 5, the primary fluid circuit 110 is illustrated by solid lines, while the secondary fluid circuit 140 is illustrated by dotted lines.

Referencing FIGS. 5 and 6, the secondary fluid is at a thermodynamic state 1 at the secondary-secondary inlet 162 as the secondary fluid enters the secondary-secondary heat exchanger 160. The secondary fluid is at thermodynamic state 2 at the secondary-secondary outlet 164. The secondary fluid undergoes expansion and reaches thermodynamic state 3. The secondary fluid at thermodynamic state 3 exchanges heat over the primary-secondary heat exchanger 150. The secondary fluid is at thermodynamic state 4 after heat exchange over the primary-secondary heat exchanger 150. The secondary fluid at thermodynamic state 4 flows over the secondary-secondary heat exchanger 160, and as the secondary fluid flows past the secondary-secondary heat exchanger 160, reaches thermodynamic state 5, after exchanging heat with the secondary fluid entering the secondary-secondary heat exchanger 160 at thermodynamic state 1.

Referencing FIGS. 5 and 6, the primary fluid is at a thermodynamic state 6 at the primary-secondary inlet 152 as the primary fluid enters the primary-secondary heat exchanger 150. The primary fluid is at thermodynamic state 7 at the primary-secondary outlet 154. The primary fluid enters the primary-primary inlet 122 at thermodynamic state 7, and leaves the primary-primary outlet 124 at thermodynamic state 8. The primary fluid undergoes expansion and reaches thermodynamic state 9. The primary fluid at thermodynamic state 9 exchanges heat with tissue. The primary fluid reaches thermodynamic state 10 after heat exchange with the tissue. The primary fluid at thermodynamic state 10 flows over the primary-primary heat exchanger 120, and reaches thermodynamic state 11 after exchanging heat with the primary fluid entering the secondary-secondary heat exchanger 160 at thermodynamic state 7.

In the example of FIGS. 5 and 6, the primary fluid and the secondary fluid may each be a cooling fluid. Thus, expansion of the primary fluid between states 8 and 9, and the expansion of the secondary fluid between states 2 and 3 each result in cooling. As seen from FIG. 6, the primary fluid entering the primary-secondary heat exchanger 150 at thermodynamic state 6 may be at a lower pressure than the secondary fluid entering the secondary-secondary heat exchanger 160 at thermodynamic state 1. However, the temperature of the primary fluid after expansion, at thermodynamic state 9 may be less than the temperature of the secondary fluid after expansion, at thermodynamic state 3. Thus, despite supplying the primary fluid at lower pressure, as a result of dual-stage cryocooling, low temperatures suitable for cryoablation (e.g., less than 190 K, for instance, about 120 K) may be achieved.

We claim:
1. A cryoablation tool, comprising:
a primary fluid circuit comprising a high pressure region for flow of a high pressure stream of a primary fluid and a low pressure region for flow of a low pressure stream of the primary fluid,
the primary fluid circuit being fluidly coupled to a distal portion of the cryoablation tool for cryogenically cooling or heating tissue surrounding the distal portion of the cryoablation tool,
the primary fluid circuit comprising a primary-primary heat exchanger configured for recuperative heat exchange between the high pressure stream of the primary fluid and the low pressure stream of the primary fluid;
a secondary fluid circuit comprising a high pressure region for flow of a high pressure stream of a secondary fluid and a low pressure region for flow of a low pressure stream of the secondary fluid,
the secondary fluid circuit comprising a secondary-secondary heat exchanger configured for recuperative heat exchange between the high pressure stream of the secondary fluid and the low pressure stream of the secondary fluid,
the secondary-secondary heat exchanger terminating in a secondary-secondary outlet; and
a primary-secondary heat exchanger configured for recuperative heat exchange between the high pressure stream of the primary fluid and the low pressure stream of the secondary fluid,
the primary-secondary heat exchanger comprising a primary-secondary inlet,
the primary-secondary heat exchanger being arranged such that the primary-secondary inlet is positioned downstream of the secondary-secondary outlet along a direction of flow of the high pressure stream of the secondary fluid,
the primary-secondary heat exchanger and the secondary-secondary heat exchanger arranged such that the low pressure stream of the secondary fluid exchanges heat with the primary fluid in the primary-secondary heat exchanger prior to exchanging heat with the high pressure stream of the secondary fluid in the secondary-secondary heat exchanger.
2. The cryoablation tool according to claim 1, wherein each of the primary-primary heat exchanger, the secondary-secondary heat exchanger and the primary-secondary heat exchanger comprises a tube having an outer wall, the outer wall of the tube comprises extensions to increase a surface area of the outer wall.

3. The cryoablation tool according to claim 1, wherein the secondary-secondary heat exchanger and the primary-secondary heat exchanger each comprises a tube that is wound in a series of turns about a tubular mandrel.

4. The cryoablation tool of claim 1, wherein the primary-primary heat exchanger is fluidly coupled with the primary-secondary heat exchanger such that the high pressure stream of the primary fluid flows through the primary-secondary heat exchanger prior to flowing through the primary-primary heat exchanger.

5. The cryoablation tool of claim 4, wherein the fluid coupling between the primary-primary heat exchanger and the primary-secondary heat exchanger is configured to fluidly isolate the low pressure stream of the primary fluid from the primary-secondary heat exchanger.

6. The cryoablation tool of claim 4, wherein the fluid coupling between the primary-primary heat exchanger and the primary-secondary heat exchanger is configured to fluidly isolate the low pressure stream of the primary fluid from the secondary-secondary heat exchanger.

7. The cryoablation tool of claim 1, wherein the flow of the low pressure stream of the primary fluid is isolated from the low pressure region of the secondary fluid circuit.

8. The cryoablation tool of claim 1, wherein the low pressure stream of the primary fluid is arranged concentrically with the low pressure flow of the secondary fluid and is physically separated therefrom.

9. The cryoablation tool of claim 1, wherein both the secondary-secondary heat exchanger and the primary-secondary heat exchanger are isolated from the low pressure region of the primary fluid circuit.

10. A cryoablation method using the cryoablation tool of claim 1, the method comprising:
supplying a primary fluid from a primary fluid source toward a distal end of the cryoablation tool via the primary fluid circuit; and
supplying a secondary fluid from a secondary fluid source toward the distal end of the cryoablation tool via the secondary fluid circuit.

11. The cryoablation method of claim 10, wherein the primary fluid circuit comprises a primary return conduit for passage of the low pressure stream of the primary fluid therethrough, and wherein the secondary fluid circuit comprises a secondary return conduit for passage of the low pressure stream of the secondary fluid, the method further comprising carrying the secondary fluid away from the distal end via the secondary return conduit.

12. The cryoablation method of claim 11, wherein carrying the primary fluid away from the distal end via the primary return conduit comprises venting the primary fluid to atmosphere, and/or wherein carrying the secondary fluid away from the distal end via the secondary return conduit comprises venting the secondary fluid to atmosphere.

13. The cryoablation method of claim 11, wherein carrying the primary fluid away from the distal end via the primary return conduit comprises returning the primary fluid to the primary fluid source, and/or wherein carrying the secondary fluid away from the distal end via the secondary return conduit comprises returning the secondary fluid to the secondary fluid source.

14. The cryoablation method of claim 11, wherein a first J-T orifice is disposed within the primary return conduit, and wherein each of the secondary-secondary heat exchanger, the primary-secondary heat exchanger, and a second J-T orifice are disposed within the secondary return conduit, the method further comprising:
cryogenically expanding the high pressure stream of the primary fluid to the low pressure stream of the primary fluid and cryogenically expanding the high pressure stream of the secondary fluid to the low pressure stream of the secondary fluid via the second J-T orifice.

15. A cryoablation tool, comprising:
a primary fluid circuit comprising a high pressure region for flow of a high pressure stream of a primary fluid and a low pressure region for flow of a low pressure stream of the primary fluid,
the primary fluid circuit being fluidly coupled to a distal portion of the cryoablation tool for cryogenically cooling or heating tissue surrounding the distal portion of the cryoablation tool,
the primary fluid circuit comprising a primary-primary heat exchanger configured for recuperative heat exchange between the high pressure stream of the primary fluid and the low pressure stream of the primary fluid;
a secondary fluid circuit comprising a high pressure region for flow of a high pressure stream of a secondary fluid and a low pressure region for flow of a low pressure stream of the secondary fluid,
the secondary fluid circuit comprising a secondary-secondary heat exchanger configured for recuperative heat exchange between the high pressure stream of the secondary fluid and the low pressure stream of the secondary fluid,
the secondary-secondary heat exchanger terminating in a secondary-secondary outlet; and
a primary-secondary heat exchanger configured for recuperative heat exchange between the high pressure stream of the primary fluid and the low pressure stream of the secondary fluid,
the primary-secondary heat exchanger comprising a primary-secondary inlet,
the primary-secondary heat exchanger being arranged such that the primary-secondary inlet is positioned downstream of the secondary-secondary outlet along a direction of flow of the high pressure stream of the secondary fluid,
the primary-secondary heat exchanger and the secondary-secondary heat exchanger arranged such that the low pressure stream of the secondary fluid exchanges heat with the primary fluid in the primary-secondary heat exchanger prior to exchanging heat with the high pressure stream of the secondary fluid in the secondary-secondary heat exchanger, and
wherein the primary fluid circuit comprises a first Joule-Thomson (J-T) orifice positioned in the distal portion of the cryoablation tool,
the first J-T orifice being fluidly coupled to the primary-primary heat exchanger via a primary supply conduit to receive the high pressure stream of the primary fluid after the high pressure stream of the primary fluid passes through the primary-primary heat exchanger,
the first J-T orifice configured to cryogenically expand the high pressure stream of the primary fluid to the low pressure stream of the primary fluid.

16. The cryoablation tool of claim 15, further comprising a primary return conduit for passage of the low pressure stream of the primary fluid therethrough, the first J-T orifice being disposed within the primary return conduit.

17. The cryoablation tool of claim 15, wherein the secondary fluid circuit comprises a second Joule-Thomson (J-T) orifice, the second J-T orifice being fluidly coupled to the secondary-secondary heat exchanger via a secondary supply conduit to receive the high pressure stream of the secondary fluid after the high pressure stream of the secondary fluid passes through the secondary-secondary heat exchanger, the second J-T orifice configured to cryogenically expand the high pressure stream of the secondary fluid to the low pressure stream of the secondary fluid.

18. The cryoablation tool of claim 17, wherein the secondary fluid circuit comprises a secondary return conduit for passage of the low pressure stream of the secondary fluid, wherein, the secondary-secondary heat exchanger, the primary-secondary heat exchanger, and the second J-T orifice are each disposed within the secondary return conduit.

19. The cryoablation tool of claim 18, wherein the secondary return conduit is fluidly isolated from the low pressure stream of the primary fluid of the primary fluid circuit.

20. The cryoablation tool according to claim 15, wherein the low pressure stream of the primary fluid and/or the secondary fluid are configured to vent to atmosphere.

* * * * *